United States Patent [19]
Mihori

[11] Patent Number: 6,063,075
[45] Date of Patent: May 16, 2000

[54] ELECTROSURGICAL APPARATUS AND SEPARATION DETECTING METHOD CAPABLE OF STABLY MONITORING SEPARATION STATE OF RETURN ELECTRODE

[75] Inventor: Takashi Mihori, Sagamihara, Japan

[73] Assignee: Olympus Optical Co., Ltd., Tokyo, Japan

[21] Appl. No.: 09/097,551

[22] Filed: Jun. 15, 1998

[30] Foreign Application Priority Data

Jun. 19, 1997 [JP] Japan ................................. 9-162685

[51] Int. Cl.$^7$ .................................................. A61B 18/16
[52] U.S. Cl. ................................ 606/35; 606/32; 128/908
[58] Field of Search .............................. 606/32, 35, 38; 128/908

[56] References Cited

U.S. PATENT DOCUMENTS

| | | |
|---|---|---|
| 4,416,276 | 11/1983 | Newton et al. . |
| 4,848,335 | 7/1989 | Manes . |
| 5,830,212 | 11/1998 | Cartmell et al. ........................ 606/35 |

FOREIGN PATENT DOCUMENTS 58-103445  6/1983  Japan .

Primary Examiner—Lee Cohen
Attorney, Agent, or Firm—Frishauf, Holtz, Goodman, Langer & Chick, P.C.

[57] ABSTRACT

An electrosurgical apparatus detects separation of a return electrode of the electrosurgical apparatus for cutting and coagulating an organic tissue from a patient. An impedance detecting section detects a contact impedance between the return electrode and the patient and generates an impedance detection signal corresponding to the contact impedance. A first discrimination section discriminates if the impedance detection signal generated by the impedance detecting section falls within a normal range of the contact impedance having predetermined upper and lower limits after the electrosurgical apparatus is powered on. When the first discrimination section detects that the impedance detection signal lies in the normal range, a storage section stores the then impedance detection signal as a reference signal. A second discrimination section discriminates if the return electrode is in an abnormal state where the return electrode is separated from the patient, based on a difference between the impedance detection signal, generated by the impedance detecting section, and the reference signal stored in the storage section.

11 Claims, 10 Drawing Sheets

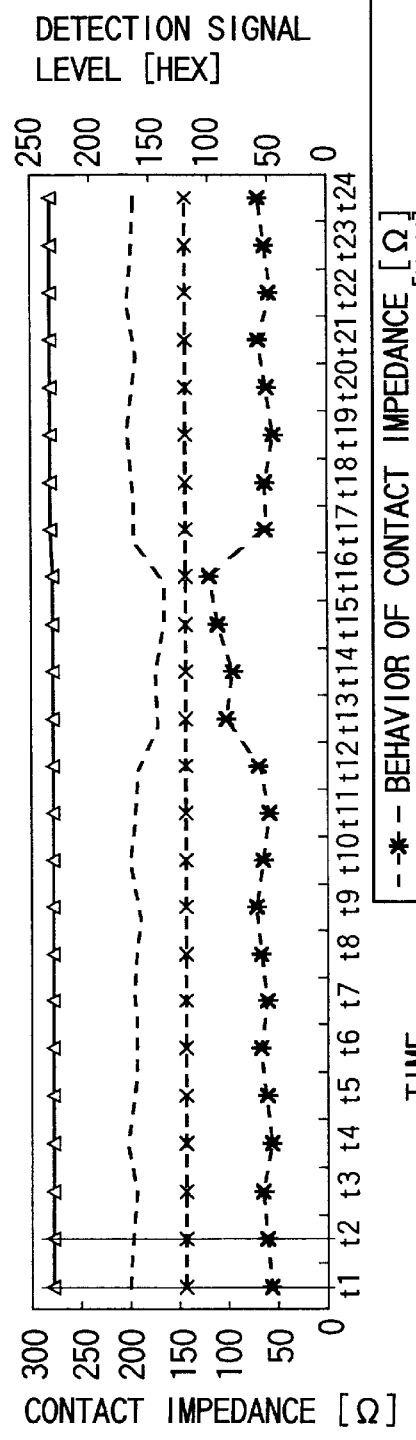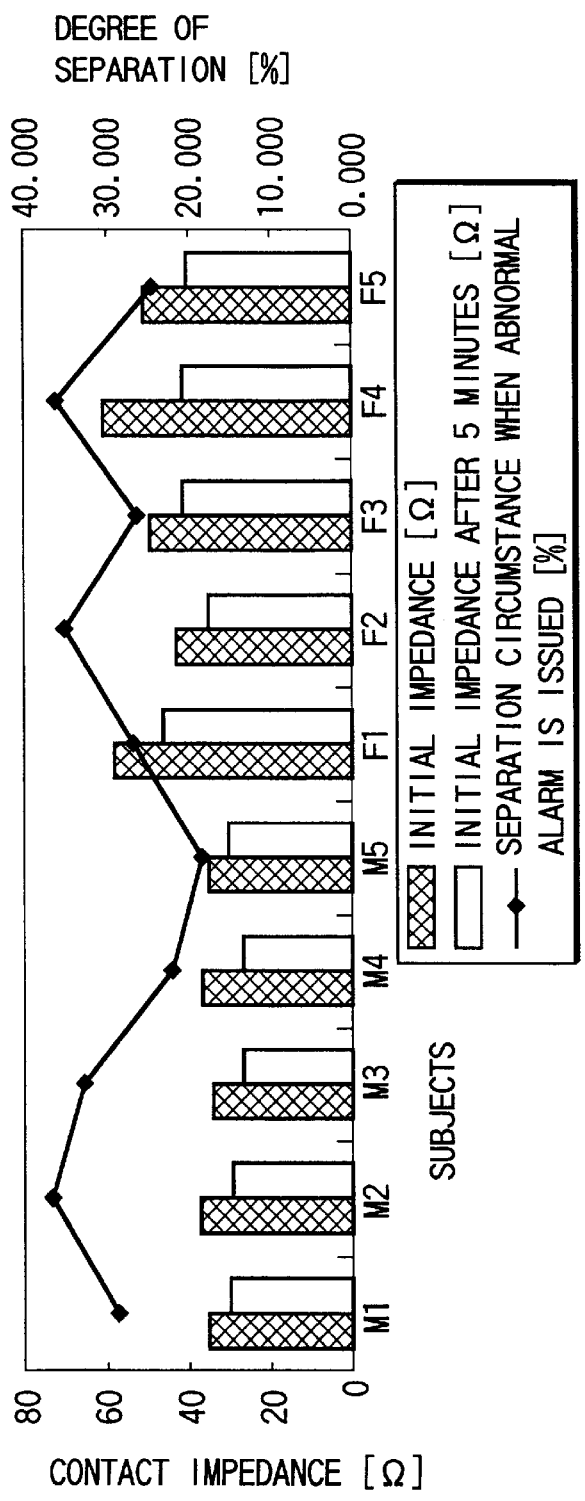
FIG. 9A
FIG. 9B

ELECTROSURGICAL APPARATUS AND SEPARATION DETECTING METHOD CAPABLE OF STABLY MONITORING SEPARATION STATE OF RETURN ELECTRODE

BACKGROUND OF THE INVENTION

The present invention relates to an electrosurgical apparatus which carries out discission and coagulation on an organic tissue or a surgical target by heat generated by high-frequency power, and, more particularly, to a return electrode separation monitor which discriminates if the return electrode of such an electrosurgical apparatus is properly attached to a patient.

Electrosurgical apparatuses are used in a variety of medical fields, such as surgery and an endoscopic treatment. FIG. 1 is a diagram showing a general structure when an operator 100 performs a treatment using an electrosurgical apparatus. In a treatment, high-frequency power generated by a high-frequency oscillator 106-1 in an electrosurgical apparatus body 106 causes a high-frequency current I to flow across a load of an organic tissue or the like of a patient 103 lying on a bed 105. Based on the Joule heat that is determined by the high-frequency current I and the resistance of the organic tissue, the tissue is vaporized or exploded by a treatment tool 101, thus ensuring discission and coagulation of the tissue.

When the above electrosurgical apparatus is used in mono-polar mode, generally, at least two electrodes are needed. One is an electrode 102 for supplying a high-frequency current to a patient (hereinafter this electrode will be called "active electrode"). The active electrode 102 in use often has a sharp shape like a needle or a blade in order to narrow the area of electrode-tissue contact and improve the current density at a surgical area.

The other electrode is a so-called return electrode (split counter electrode plate) 104 that collects the high-frequency current, which flows through a patient from the active electrode 102, and returns the high-frequency current to the electrosurgical apparatus body 106. As this return electrode 104 also serves to prevent a burn at a portion of contact to a tissue, the return electrode 104, unlike the active electrode 102, is shaped to have a wide area to reduce the current density at the contact. If the return electrode 104 is not in proper contact to a patient, local current concentration may cause a burn.

Recently therefore has been proposed a return electrode separation monitor and method in which the return electrode 104 is constructed by two conductors and which previously discriminate if the return electrode 104 is properly attached to a patient by detecting an AC-like impedance between the two conductors.

One conventional return electrode separation detecting method detects an AC-like contact impedance using the property of a transformer such that the impedances appearing on the primary winding and the secondary winding is determined by the winding ratio of the transformer, and compares a detection signal according to the contact impedance with a given threshold value for abnormality determination to determine an abnormality.

According to this return electrode separation detecting method, however, the characteristic of an AC impedance detecting section is determined by the characteristics of the transformer so that a signal corresponding to the contact impedance to be detected varies due to a variation in various characteristics of the transformer. Further, the contact impedance between the return electrode and a patient is actually as low as several tens of ohms and the contact impedance when the return electrode is gradually separated varies in the order of several ohms. This makes it practically very difficult to detect the contact impedance by the transformer alone, not to mention the large variation of the contact impedance.

If as idealistic a transformer as possible is used, a contact impedance which varies very slightly may be detected reliably. Practically, however, it is very hard to manufacture such an idealistic transformer, which, if manufactured, would lead to an increased cost.

When abnormality determination is carried out with a predetermined, specific fixed threshold value, the area of separation of the return electrode up to the point where an abnormality is determined differs depending on subject persons because the contact impedance significantly varies person by person. In an extreme case, even if the return electrode is fully in contact with a person who has a high contact impedance, an alarm may be issued, hindering a procedure. For a person who has a low contact impedance, on the other hand, the area of separation of the return electrode up to the point where an abnormality is determined becomes large, resulting in a lower detection accuracy which makes it more likely to cause a burn.

In short, the prior art has a difficulty in detecting the contact impedance which varies in the order of several ohms, has a large variation in the detected signal itself, cannot enhance the detection precision, and suffers a significant person-dependent variation in the area of separation of the return electrode up to the point where an abnormality is determined because abnormality determination is performed on the contact impedance, which considerably differs from one person to another, based on a predetermined, specific threshold value (fixed). Depending on a patient, it may not be determined as abnormal even when the area of separation becomes large.

BRIEF SUMMARY OF THE INVENTION

Accordingly, it is an object of the present invention to provide an electrosurgical apparatus and a return electrode separation monitor which are capable of stably monitoring the separation state of the return electrode without depending on a variation in a detected signal or a difference in contact impedance from one patient to another.

To achieve the above object, according to the first aspect of this invention, an electrosurgical apparatus for detecting separation of a return electrode of the electrosurgical apparatus for cutting and coagulating an organic tissue from a patient, comprises:

an impedance detecting section for detecting a contact impedance between the return electrode and the patient and generating an impedance detection signal corresponding to the contact impedance;

a first discrimination section for discriminating if the impedance detection signal generated by the impedance detecting section falls within a normal range of the contact impedance having predetermined upper and lower limits after the electrosurgical apparatus is powered on;

a storage section for, when the first discrimination section detects that the impedance detection signal lies in the normal range, storing the then impedance detection signal as a reference signal; and a second discrimination section for discriminating if the return electrode is in an abnormal state where the return electrode is separated from the patient, based on a difference between the impedance detection signal, generated by the impedance detecting section, and the reference signal stored in the storage section.

According to the second aspect of this invention, a return electrode separation monitor is adapted to be connected to an electrosurgical apparatus for detecting separation of a return electrode of the electrosurgical apparatus for cutting and coagulating an organic tissue from a patient. The monitor comprises an impedance detecting section for detecting a contact impedance between the return electrode and the patient and generating an impedance detection signal corresponding to the contact impedance;

a first discrimination section for discriminating if the impedance detection signal generated by the impedance detecting section falls within a normal range of the contact impedance having predetermined upper and lower limits after the electrosurgical apparatus is powered on;

a storage section for, when the first discrimination section detects that the impedance detection signal lies in the normal range, storing the then impedance detection signal as a reference signal; and a second discrimination section for discriminating if the return electrode is in an abnormal state where the return electrode is separated from the patient, based on a difference between the impedance detection signal, generated by the impedance detecting section, and the reference signal stored in the storage section.

According to the third aspect of this invention, a method of detecting separation of a return electrode of the electrosurgical apparatus for cutting and coagulating an organic tissue from a patient, comprising:

an impedance detecting step of detecting a contact impedance between the return electrode and the patient and generating an impedance detection signal corresponding to the contact impedance;

a first discrimination step of discriminating if the generated impedance detection signal falls within a normal range of the contact impedance having predetermined upper and lower limits after the electrosurgical apparatus is powered on;

a storage step of, when it is detected that the impedance detection signal lies in the normal range, storing the then impedance detection signal as a reference signal; and a second discrimination step of discriminating if the return electrode is in an abnormal state where the return electrode is separated from the patient, based on a difference between the impedance detection signal, generated in the impedance detecting step, and the reference signal stored in the storage step.

Additional object and advantages of the invention will be set forth in the description which follows, and in part will be obvious from the description, or may be learned by practice of the invention. The object and advantages of the invention may be realized and obtained by means of the instrumentalities and combinations particularly pointed out hereinbefore.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 9A is a diagram for exemplarily illustrating the return electrode separation monitor detection process, with the time taken on the horizontal scale while taking contact impedances and hexadecimal values representing digital data of detection signal levels corresponding to the contact impedance on the vertical scale;

FIG. 9B is a diagram representing a minute change in contact impedance; and

DETAILED DESCRIPTION OF THE INVENTION

Preferred embodiments of the present invention will now be described with reference to the accompanying drawings.

Figure 1:
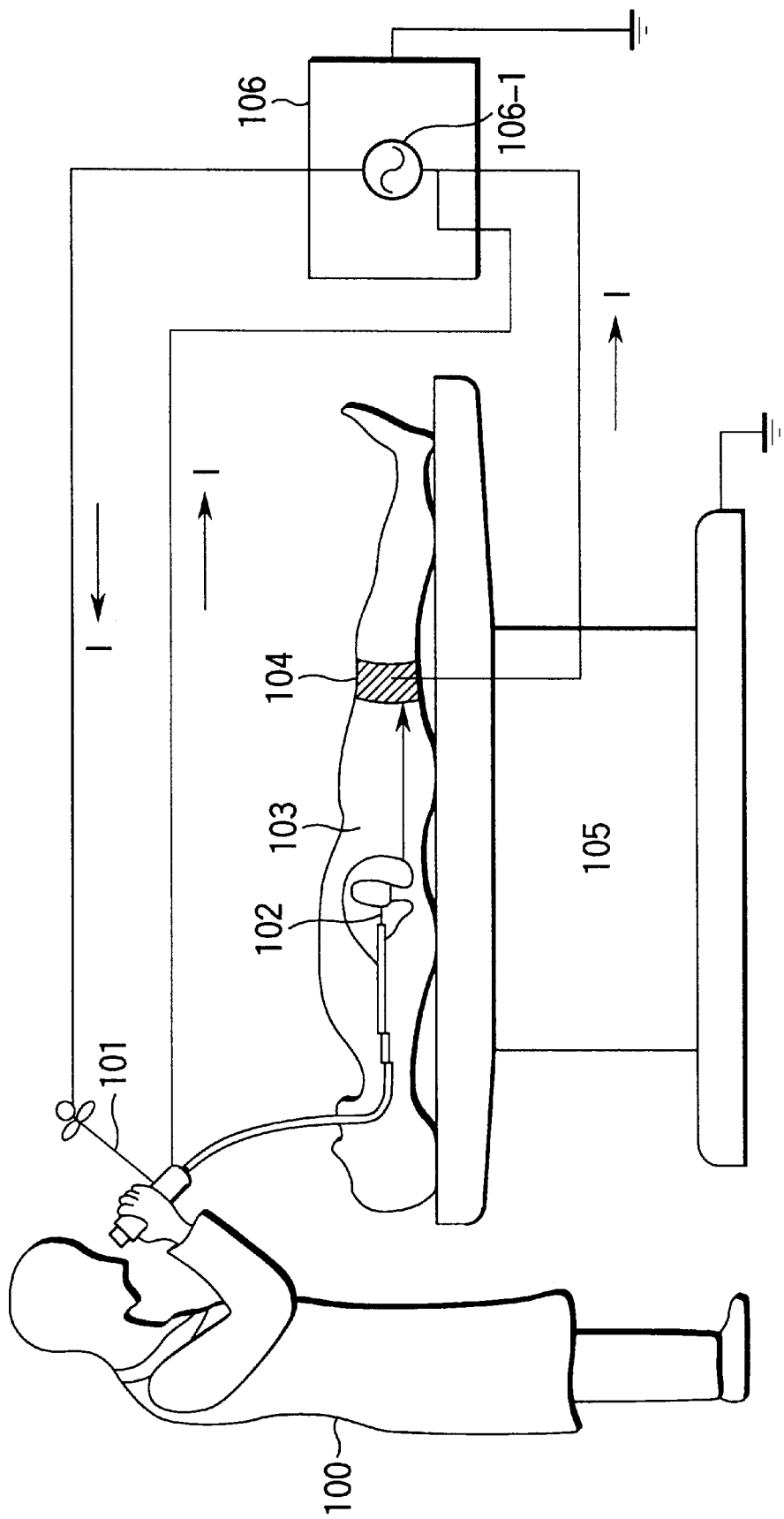
FIG. 1 is a diagram showing a general structure at the time of treating a patient with an electrosurgical apparatus.
Figure 2:
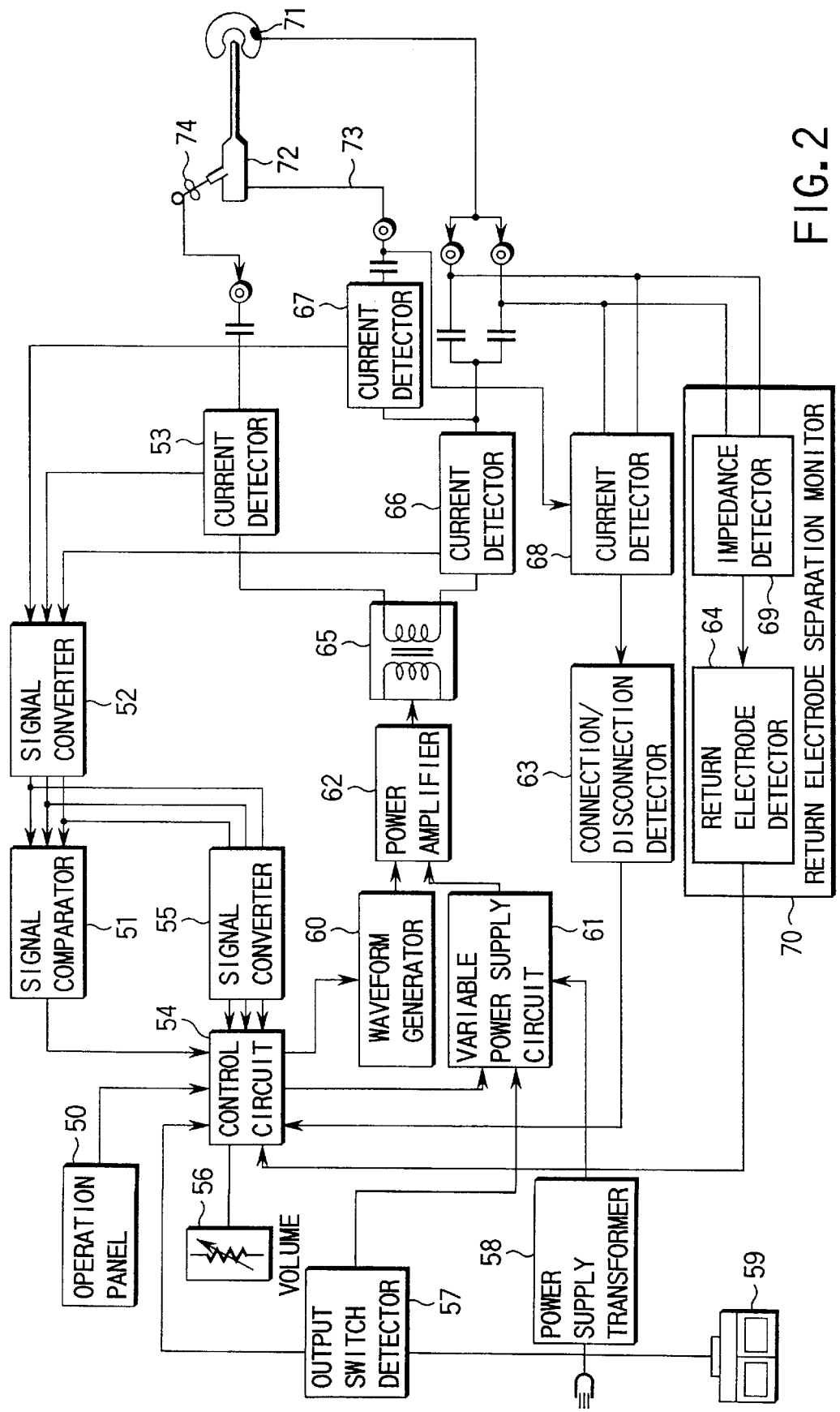
FIG. 2 is a block diagram depicting the internal structure of an electrosurgical apparatus.

FIG. 2 is a block diagram depicting the internal structure of an electrosurgical apparatus. In FIG. 2, a control circuit 54 is a main control circuit for controlling the operations of the individual sections. An output switch detector 57 discriminates the ON/OFF status of an output switch 59, and sends a detection signal to the control circuit 54. Based on this detection signal, the control circuit 54 executes output control (ON/OFF of the output) on high-frequency power. A volume 56 is for changing the volume of the output that is generated at the time of outputting high-frequency power. An operation panel 50 is a user interface for allowing a user to select a set value for the high-frequency output, an output mode and so forth.

A waveform generator 60 generates a pulse waveform according to the output mode set via the operation panel 50, and a power amplifier 62 is driven with this pulse waveform. A variable power supply circuit 61 generates a DC supply voltage according to the output set value set through the operation panel 50, and supplies the voltage to the power amplifier 62. This variable power supply circuit 61 is supplied with power which is acquired by insulating the input voltage from a commercially available voltage supply by means of a power supply transformer 58.

The power amplifier 62 is an inverter circuit which operates on the pulse waveform sent from the waveform generator 60 and the output voltage of the variable power supply circuit 61 to generate high-frequency power. A mono-polar output transformer 65 is an insulating transformer which supplies the high-frequency power generated by the power amplifier 62 in an insulated manner to a patient.

A current detector 53 detects a high-frequency output current to be supplied to a treatment tool 74. The current detector 67 detects a high-frequency output current to be supplied to an endoscope 72 via an endoscope cord 73. A current detector 66 detects a current from a return electrode 71. A signal converter 52 converts the current, actually detected by any of the current detectors 53, 66 and 67, to a DC signal (analog signal). A signal comparator 51 compares this analog signal with a reference value to determine if a high-frequency current flows in an unintended path. A signal converter 55 converts the DC signal (analog signal), converted by the signal converter 52, to a digital signal, and sends the digital signal to the control circuit 54.

A current detector 68 detects a current representing the disconnection/connection of the return electrode 71 and the endoscope cord 73, and supplies the current to a connection/disconnection detector 63. This connection/disconnection detector 63 monitors the connected status of the return electrode 71 and the endoscope cord 73 and informs the control circuit 54 of the result.

An impedance detector 69 monitors and detects the impedance of a tissue which is in contact with a plurality of conductors when the return electrode 71 is in use. A return electrode detector 64 monitors the separation state of the return electrode 71 in accordance with the detection signal that has been detected by the impedance detector 69. The impedance detector 69 and the return electrode detector 64 constitute a return electrode separation monitor 70 which will be discussed later.

Figure 3:
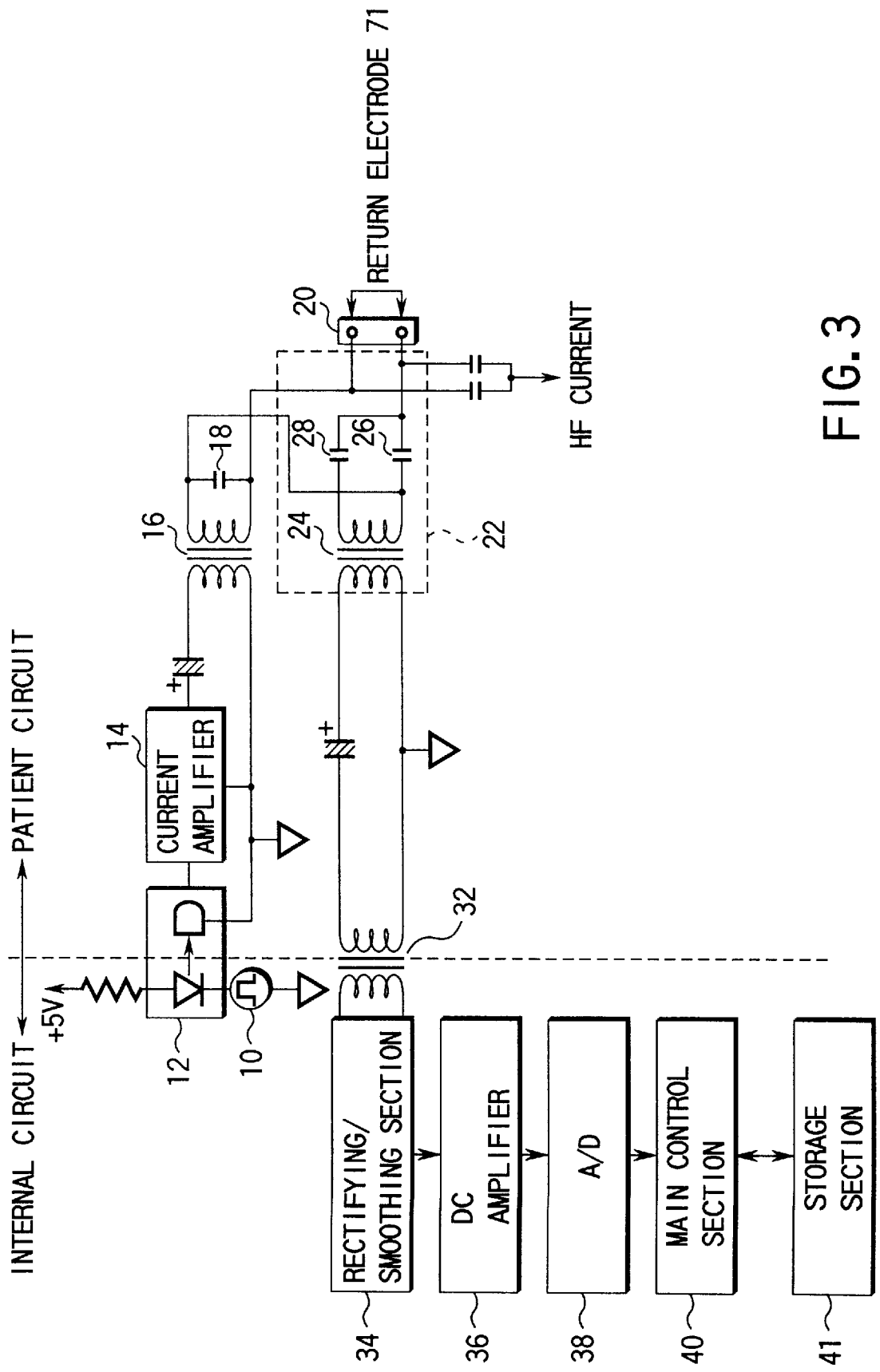
FIG. 3 is a diagram illustrating the structure of a return electrode separation monitor according to a first embodiment of this invention.

FIG. 3 is a diagram illustrating the structure of a return electrode separation monitor according to a first embodiment of this invention. The operation of this structure will be discussed below with reference to the aforementioned drawings. An AC power supply 10 for impedance detection generates a rectangular wave of, for example, 100 kHz in the internal circuitry of the electrosurgical apparatus. This rectangular wave is transmitted into a patient circuit by a photocoupler 12. At this time, the output signals of the AC power supply 10 and the photocoupler 12 are pulse signals in phase with each other.

The pulse signal transmitted in the patient circuit by the photocoupler 12 is amplified by a current amplifier 14, which is comprised of a push-pull amplifier or the like, and is then supplied between two conductors (not shown), which constitute the return electrode 71, via an insulating transformer 16. A capacitor 18 connected in parallel to the secondary winding of the insulating transformer 16 constitutes, together with the secondary winding of this transformer 16, a resonance circuit, and is provided to transform a signal for detecting the impedance between the two conductors (hereinafter called "contact impedance") into a sine wave.

Figure 4A:
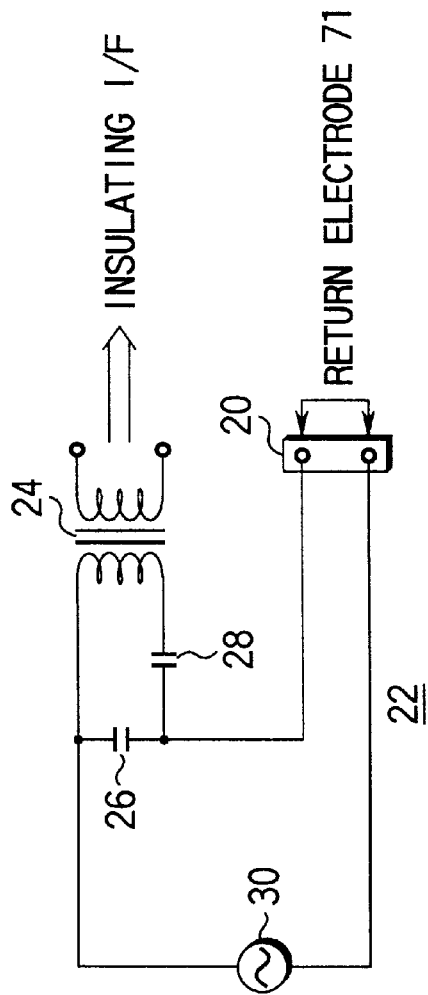
FIG. 4A is an equivalent circuit diagram showing a contact impedance detecting section extracted from FIG. 3.

The return electrode 71 is connected to a return electrode connector 20 on the main body, and the detection signal of the contact impedance is detected by a contact impedance detector 22. This contact impedance detector 22 comprises a transformer 24, capacitors 26 and 28, and the contact impedance between the return electrode 71, connected to the return electrode connector 20, and the patient. This contact impedance detector 22, when redrafted for easier understanding, has a structure as shown in FIG. 4A. The contact impedance 22 is so designed as to transmit the sinusoidal signal (AC power supply 30) to the secondary winding of the transformer 24 in the form of a voltage-divided value acquired by an AC impedance (fixed value) of the parallel resonance circuit of the primary winding of the transformer 24 and the capacitors 26 and 28 and an AC impedance in the return electrode connector 20 or the contact impedance.

Figure 4B:
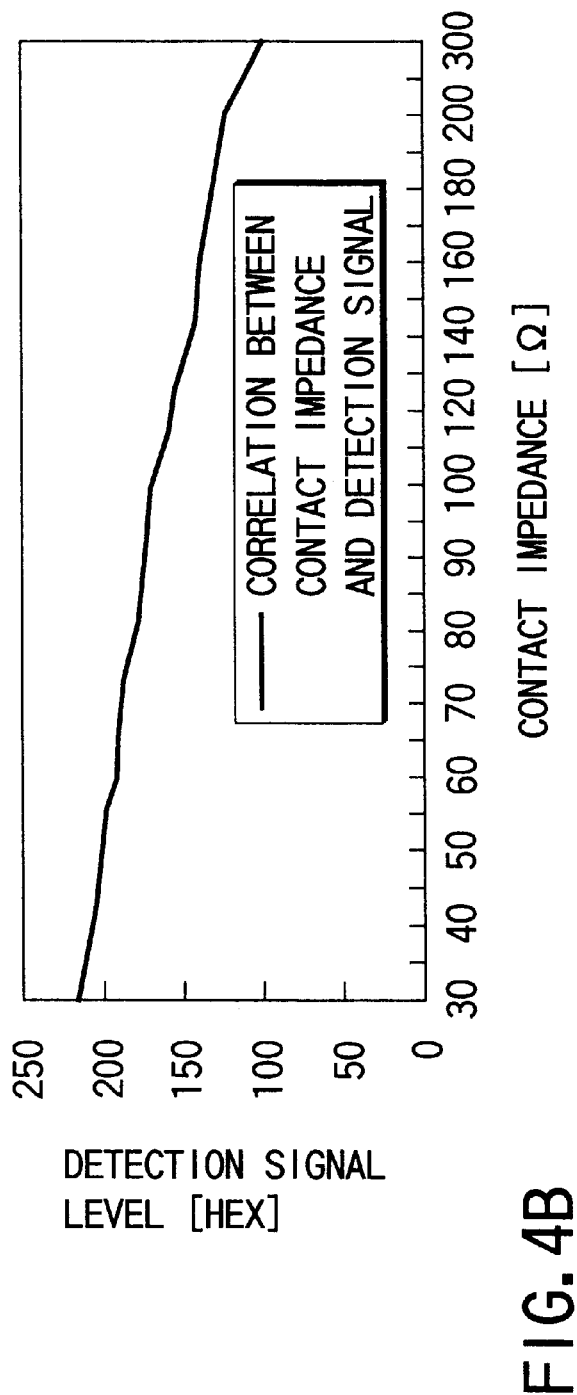
FIG. 4B is a diagram showing a relationship between a contact impedance and the level of a contact impedance detection signal.

As apparent from the above, because the signal corresponding to the contact impedance is determined by the voltage-divided value by the AC impedance of the parallel resonance circuit and the contact impedance, the level of the detection signal changes linearly in accordance with a change in contact impedance as shown in FIG. 4B, thus ensuring linear detection of the contact impedance.

The AC signal (sinusoidal signal) transmitted to the secondary winding of the transformer 24 is further transmitted to the internal circuit via a transformer 32. That is, the transformers 24 and 32 also serve as an insulating interface for transmitting an AC-like contact impedance detection signal to the internal circuit while insulating the signal.

The sinusoidal contact impedance detection signal transmitted to the internal circuit via such an insulating interface is converted by a rectifying/smoothing section 34 in the internal circuit to a DC signal which is then amplified to a predetermined level by a DC amplifier 36. The amplified DC signal is then converted by an A/D converter 38 to a digital signal, which is sent to a main control section 40. This main control section 40 detects whether or not the return electrode 71 is separated by comparing the fetched digital signal with a reference value stored in a storage section 41 when it has been determined as normal at the time of initial detection.

Figure 5:
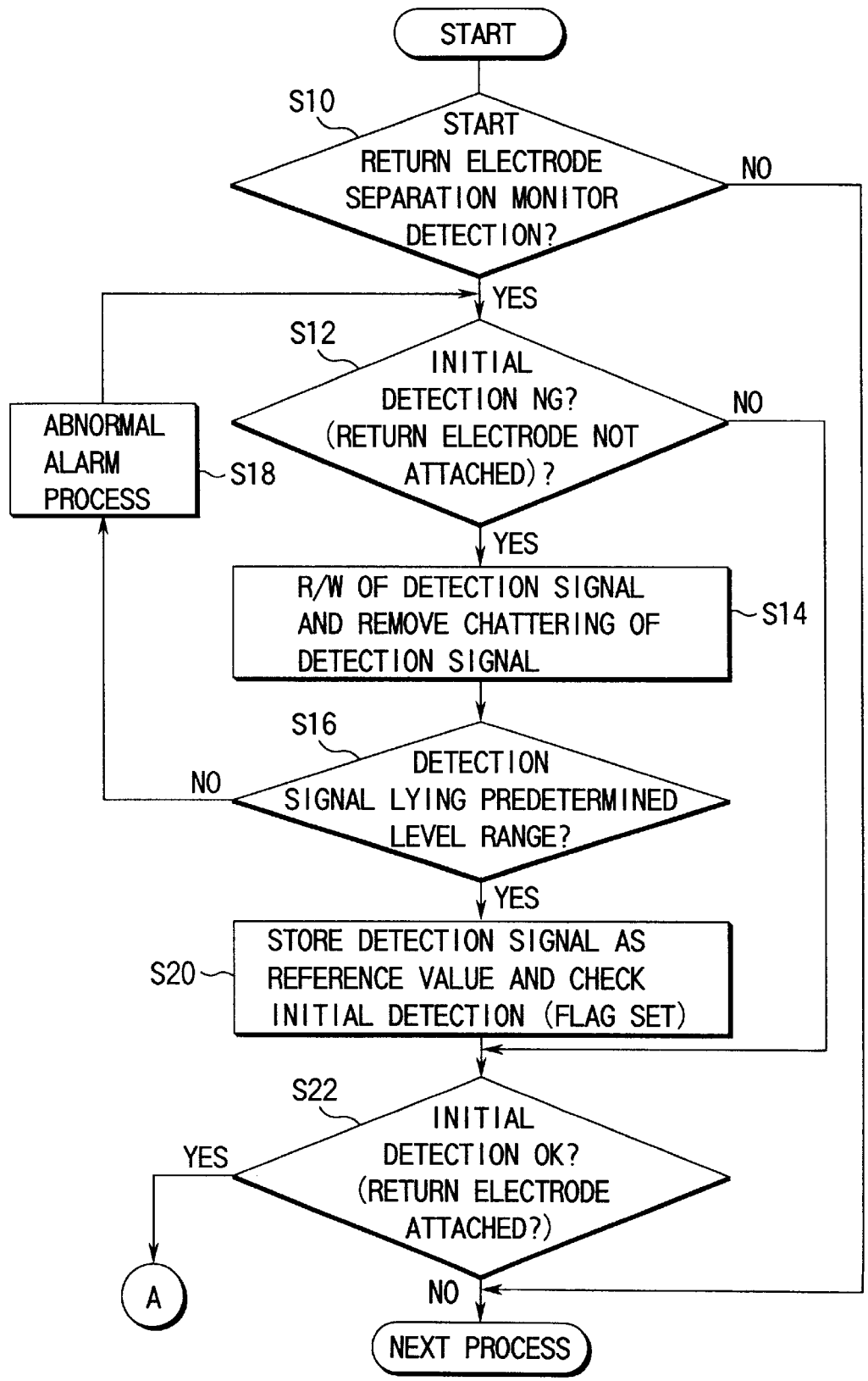
FIG. 5 is a diagram illustrating a first part of a series of flowcharts for a return electrode separation monitor detection process which is executed by a main control section in FIG. 3.
Figure 6:
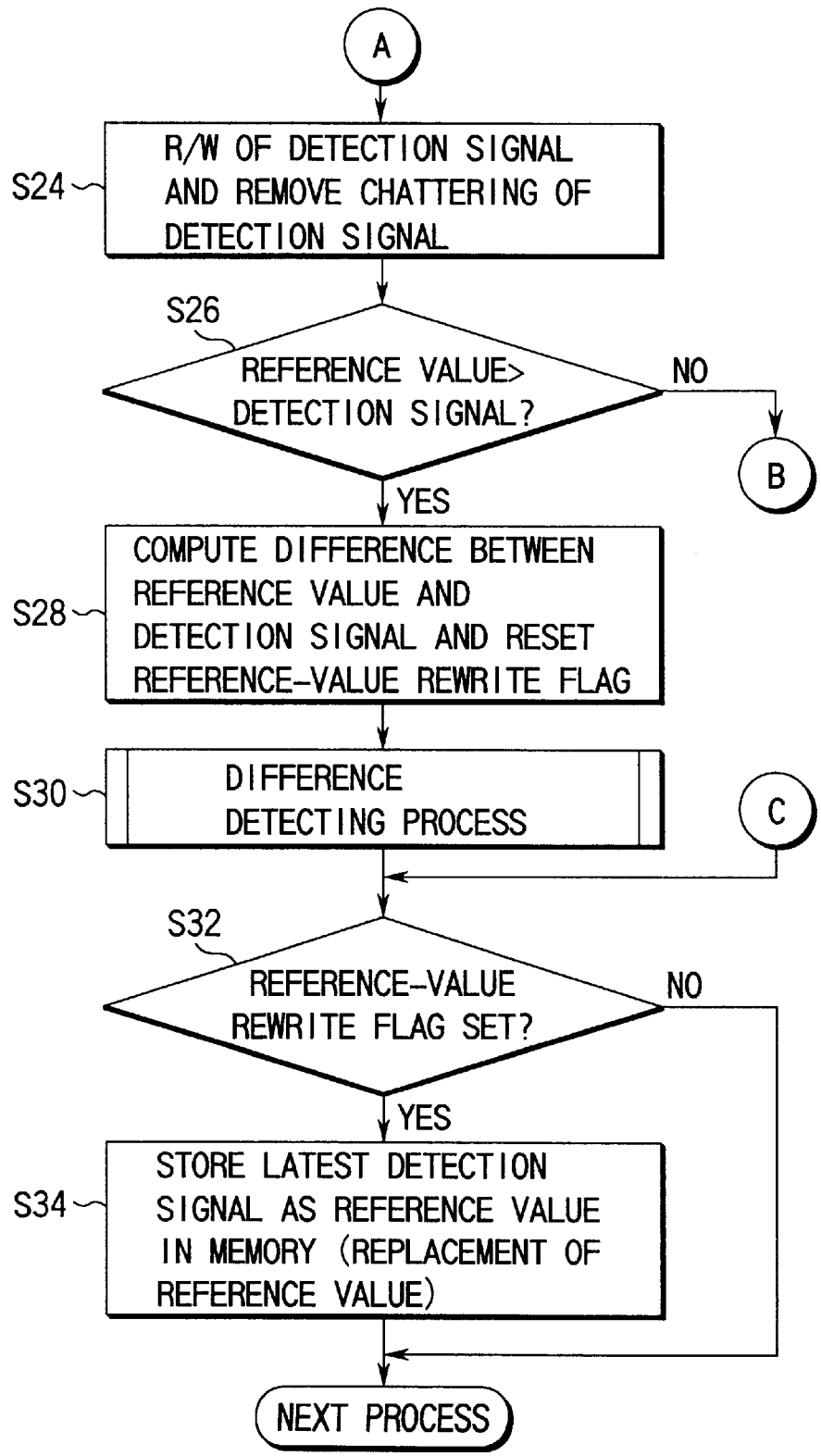
FIG. 6 is a diagram illustrating a second part of the series of flowcharts for the return electrode separation monitor detection process which is executed by the main control section in FIG. 3.
Figure 7:
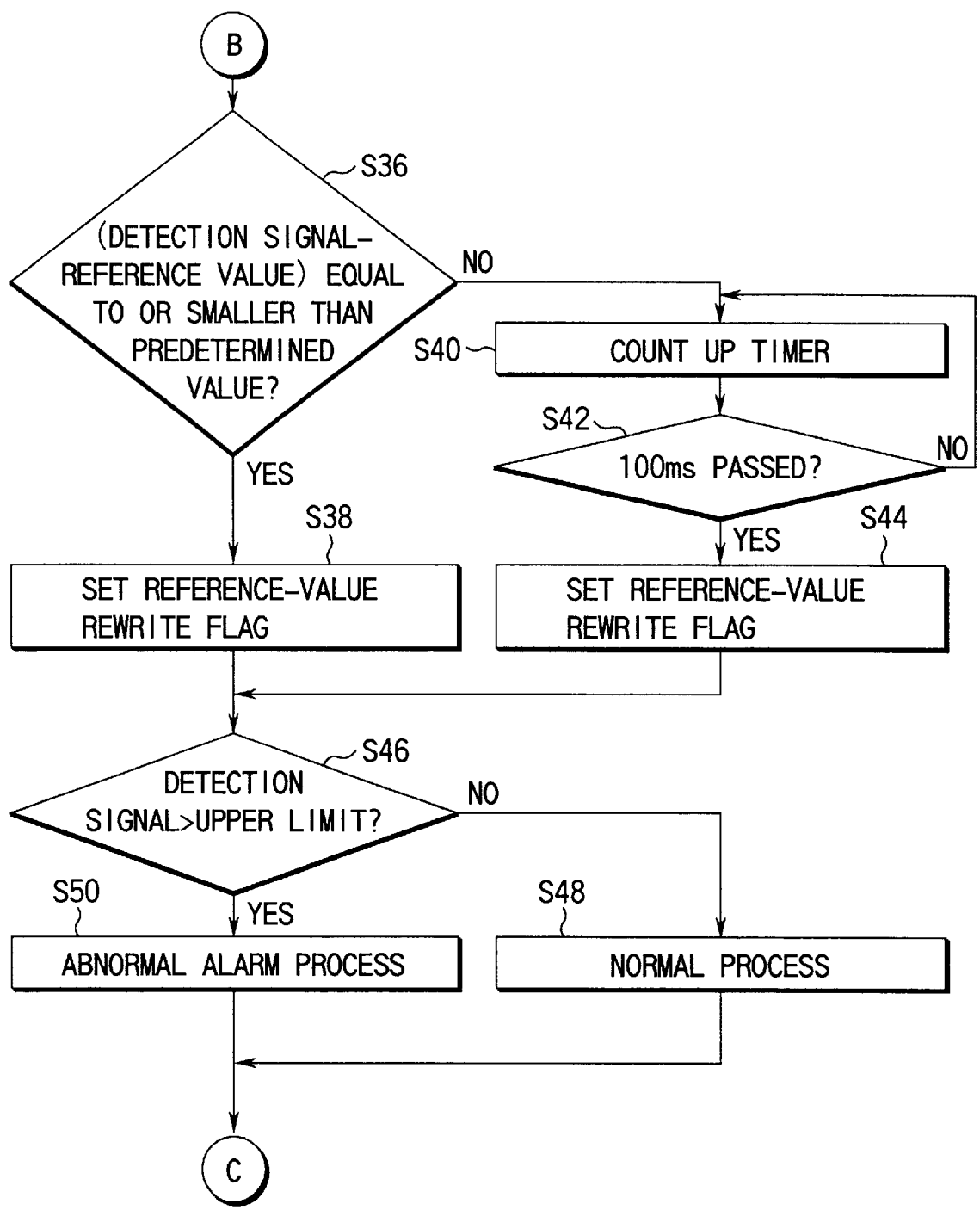
FIG. 7 is a diagram illustrating a third part of the series of flowcharts for the return electrode separation monitor detection process which is executed by the main control section in FIG. 3.

FIGS. 5 through 7 present a series of flowcharts for the return electrode separation monitor detection process which is executed by the main control section 40.

When the return electrode separation monitor detection process starts (step S10), first, initial detection is performed to detect if the return electrode 71 is in contact with a patient. In this initial detection, first, it is discriminated if the return electrode 71 is attached from an initial detection flag (step S12). Specifically, if the process is the second or later return electrode separation monitor detection process, the initial detection has already been carried out and the initial detection flag has been set, so that the subsequent initial detection process is skipped. When the initial detection flag is not set, or when the return electrode 71 is not attached, the contact impedance detection signal is read and is subjected to data processing like chattering elimination or the like (step S14), and it is determined of the processed contact impedance detection signal falls within a predetermined level range (step S16). That is, it is determined if the contact impedance lies within a resistance range having predetermined upper and lower limits. When the contact impedance does not lie within the resistance range, it is determined that the return electrode 71 is not attached and an alarm is issued (step S18), after which the flow returns to the step S12 to repeat the above processing.

When the contact impedance lies within the resistance range, the contact impedance detection signal is stored as a reference value in the storage section 41 and the initial detection flag is set (step S20). Then, whether or not the return electrode 71 is attached is discriminated from the initial detection flag (step S22). When the return electrode 71 is not attached, this return electrode separation monitor detection process is terminated and the flow goes to a next process.

When the return electrode 71 is attached, on the other hand, the separation status is monitored through a difference detecting process.

That is, the contact impedance detection signal is converted to digital data through the above-described process as needed, then is fetched into the main control section 40 to be subjected to data processing such as chattering elimination (step S24). The contact impedance detection signal fetched into the main control section 40 is compared with the reference value that was stored in the storage section 41 when it was determined as normal at the time of the initial detection (step S26). When the contact impedance detection signal is smaller than the reference value, the difference between the reference value and the contact impedance detection signal is computed and a reference-value rewrite flag is reset (step S28). Then, the difference detecting process is carried out (step S30).

Figure 8:
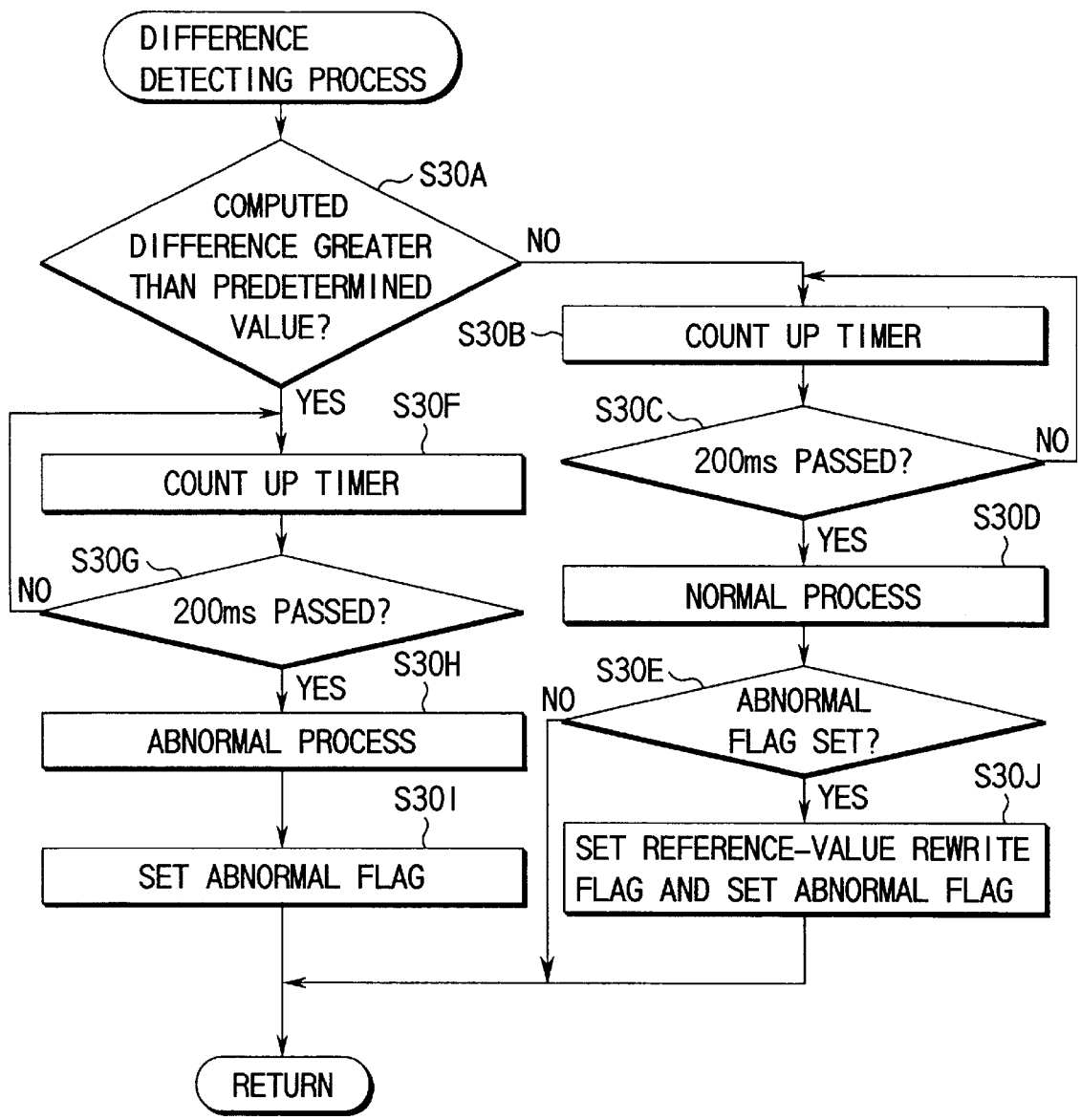
FIG. 8 is a flowchart for a difference detecting process in FIG. 6.

In the difference detecting process, as shown in FIG. 8, it is determined if the difference computed in the step S28 is greater than a predetermined value (step S30A), and if the former is not greater than the latter, a normal process is executed (step S30D) after waiting for 200 ms by means of a timer (steps S30B and S30C). The "normal process" is a process which, for example, informs that the return electrode 71 is properly attached to a patient. Then, it is discriminated if an abnormal flag is set (step S30E), and if this flag is not set, the flow returns to an upper flowchart.

When the flow returns to the upper flowchart, it is then determined if the reference-value rewrite flag is set (step S32). When the reference-value rewrite flag is not set, this return electrode separation monitor detection process is terminated and the flow proceeds to a next process.

When it is determined in step S30A in the difference detecting process that the computed difference is greater than the predetermined value, an abnormal process is executed (step S30H) after waiting for 200 ms by means of the timer (steps S30F and S30G). Accordingly, an operator can know that the return electrode 71 is not properly attached to the patient. Then, the abnormal flag is set (step S30I) and the flow returns to an upper flowchart.

When the flow returns to the upper flowchart, it is then determined in the step S32 if the reference-value rewrite flag is set as mentioned above. As the reference-value rewrite flag is not set in this case too, this return electrode separation monitor detection a process is terminated and the flow proceeds to a next process.

As this return electrode separation monitor detection process is regularly repeated, the difference detecting process is performed and it is determined in step S30A that the computed difference is not greater than the predetermined value or has returned to the normal status, the processing from step S30B to step 30D is executed after which it is determined in step S30E that the abnormal flag is set because the abnormal flag has been set in the step. S30I. In this case, the reference-value rewrite flag is set and the abnormal flag is reset (step S30J) after which the flow returns to an upper flowchart.

When the flow returns to an upper flowchart in this manner, therefore, it is determined that the reference-value rewrite flag is set. In this case, the latest contact impedance detection signal is stored as a new reference value in the storage section 41, i.e., replacement of the reference value is performed (step S34). Then, this return electrode separation monitor detection process is terminated and the flow proceeds to a next process.

As the return electrode separation monitor detection process is regularly repeated and the computed difference becomes greater than the predetermined value, it is determined that the separation area of the return electrode 71 has become large so that an alarming process is executed. When the abnormal state, once determined as such in the difference detecting process, is returned to the normal state again later, the then detected contact impedance detection signal is written as a new reference value for detecting a difference from the contact impedance detection signal as needed.

Note that the timer-measured wait in the steps S30C and S30G is inserted to stabilize the operation.

When the contact impedance detection signal is determined as equal to or greater than the reference value in the step S26, it is then determined if the contact impedance detection signal minus the reference value is equal to or smaller than a predetermined value (step S36). When the former is equal to or smaller than the predetermined value, the reference-value rewrite flag is set (step S38).

When the contact impedance detection signal minus the reference value is greater than the predetermined value, the reference-value rewrite flag is set (step S44) after waiting for 100 ms measured by the timer (steps S40 and S42). The timer-measured wait of 100 ms is provided to cope with a case where the contact impedance detection signal suddenly changes due to noise or the like. That is, if the contact impedance detection signal has suddenly changed, it is expected that the contact impedance detection signal returns to the normal range in 100 ms, so that the reference value is prevented from being replaced with the suddenly changed value in the reference value replacing process in step S34, which would otherwise take place due to the set reference-value rewrite flag.

When the reference-value rewrite flag is set in step S38 or S44 in this manner, it is then determined if the contact impedance detection signal goes beyond the predetermined upper limit (step S46). When the contact impedance detection signal has not exceeded the upper limit, a normal process is carried out (step S48) after which the flow moves to the step S32. When the contact impedance detection signal has exceeded the upper limit, on the other hand, an alarming process is carried out (step S50) after which the flow moves to the step S32.

As it is determined in the step S32 that the reference-value rewrite flag is set, the latest contact impedance detection signal is stored as a new reference value in the storage section 41 (step S34). Then, this return electrode separation monitor detection process is terminated and the flow proceeds to a next process.

When the contact impedance detection signal becomes higher than the reference value stored at the previous stage, the then detected contact impedance detection signal is written as a new reference value for difference detection as needed.

The return electrode separation monitor detection process which has been explained with reference to the flowcharts is exemplarily represented by the graph in FIG. 9A which shows the time taken on the horizontal scale while taking contact impedances and hexadecimal values representing digital data of detection signal levels corresponding to the contact impedance on the vertical scale.

First, in a period from time t1 to time t11, the contact impedance detection signal and the level of its detection signal change with time, not much though. Between time t12 to time t13, however, the contact impedance detection signal rises drastically. This implies that the impedance detector 71 nearly comes off the patient. How much the return electrode 71 is separated then is discriminated from the difference between the reference value and the detection signal. In other words, when the inclination of a change in contact impedance detection signal in FIG. 9A becomes equal to or above a predetermined level, it is determined as abnormal.

While the area of contact between the return electrode 71 and the patient does not change, however, the contact impedance detection signal varies very slightly. This is seen from a graph in FIG. 9B. M1 to M5 on the horizontal scale in FIG. 9B represent male subjects (five), and F1 to F5 female subjects (five), and the bars on the left side represent the contact impedance immediately after the return electrode 71 contacts the subjects while the right bars represent the contact impedance when five minutes passed after the return electrode 71 has contacted the subjects.

As apparent from the graph in FIG. 9B, the contact impedance upon passage of five minutes is lower for any subject than the contact impedance immediately after contact is made.

In other words, the contact impedance is closely related to the wet status of the gel on the return electrode 71 or the wet status of the patient's body surface, and as the wet statuses vary with time, the difference detecting process may not work properly if the reference value that was stored in the storage section 41 when it is determined as normal in the initial detection is held the same while the apparatus is in use.

Even when the abnormal state, once determined so in the difference detecting process, is returned to the normal state again later, the difference detecting process may not work properly if the reference value previously stored differs from the value of the contact impedance detection signal.

According to this invention, therefore, the reference value for detecting a difference from the contact impedance detection signal is set in such a way that (1) when the level of the contact impedance detection signal becomes higher than the level of the reference value stored at the previous stage and (2) when the abnormal state, once determined so in the difference detecting process, is returned to the normal state again later, the contact impedance detection signal detected at each occasion is written as a new reference value for difference detection.

With the above-described structure, the operation of the separation detecting function was actually inspected on ten subjects (the same as mentioned earlier). The test was conducted in such a way that the return electrode 71 was gradually separated from each patient along the lengthwise direction of the return electrode 71 when five minutes passed after full contact of the return electrode 71 to the patient had been established. Then, the length of the separated portion when an alarm was issued was measured to measure how much the return electrode 71 was separated with respect to the entire lengthwise length of the return electrode 71 when the alarm was generated. The results of the test are shown by the graph in FIG. 9B.

FIG. 9B shows that, for the ten subjects, the alarm actually started when 20 to 35% of the entire return electrode 71 was separated, and shows that abnormal separation can reliably be detected even with respect to a contact impedance having a large variation.

Further, it is confirmed that this embodiment is free of the problems of the prior art, such that an alarm is issued even when the return electrode is full contact with a patient or an alarm is not generated even when the separation area becomes large.

With the return electrode separation monitor for an electrosurgical apparatus designed and operated as explained above, the following advantages can be obtained.

(1) The separation area of the return electrode is monitored by a difference between contact impedance detection signals or the rate of a change therein and the reference value for computing the difference is automatically set to the optimal value by a user, so a variation in separation area at the time of generating an alarm can be reduced even when the contact impedance has a large person-dependent change.

(2) Because the reference signal level for computing the difference is rewritten to a latest value as needed when the contact impedance detection signal becomes greater than the reference value stored in the storage section 41 at the previous stage and/or when the abnormal state, once determined as such in the difference detecting process, is returned to the normal state again later, it is possible to cope with the time-varying contact impedance detection signal and reliably detect abnormal separation without malfunctioning even when the abnormal state is returned to the normal state.

(3) As the impedance detector 22 detects the contact impedance based on the voltage division by the fixed AC impedance that is determined by the parallel resonance circuit and the contact impedance, the detection signal linearly changes with respect to a change in the contact impedance.

In view of the above, it is possible to eventually reduce a person-dependent variation and improve the detection precision of the return electrode separation monitor.

A second embodiment of this invention will now be described. When the return electrode separation monitor is activated to execute abnormality discrimination while a treatment is actually performed or when a procedure is about to start, high-frequency power is stopped then, disabling continuation of the treatment. In this case, the return electrode may be left cut into the tissue and stuck there, causing the affected portion to bleed, or disabling further procedure of an emergency treatment.

The second embodiment is designed to allow a user to intentionally stop the return electrode separation monitor in emergency so that the above problem is overcome to ensure the required procedure.

Figure 10:
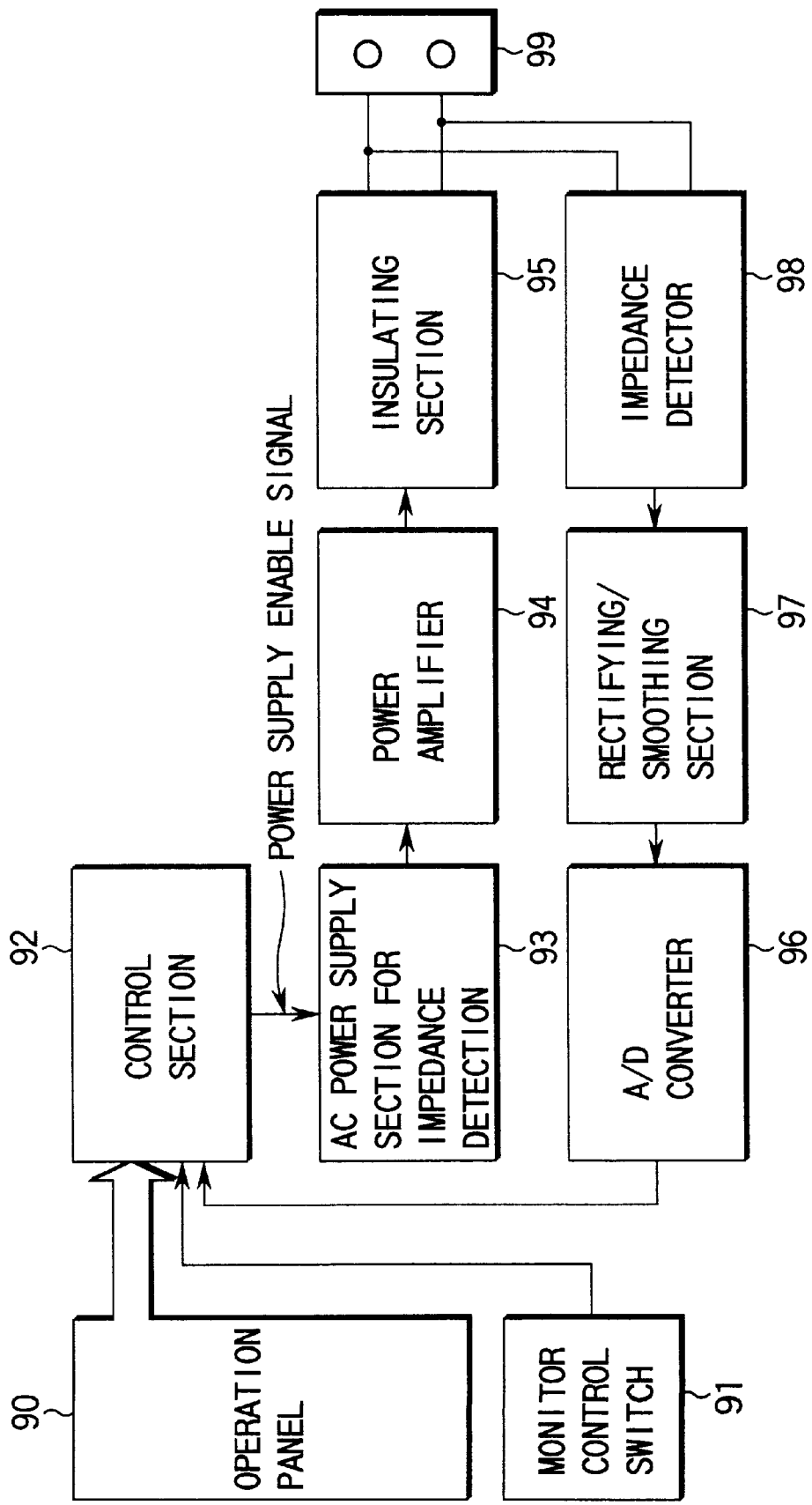
FIG. 10 is a diagram depicting the structure of a return electrode separation monitor according to a second embodiment of the invention.

FIG. 10 is a diagram depicting the structure of a return electrode separation monitor according to the second embodiment of the invention, which comprises a control section 92, an AC power supply 93 for impedance detection, a current amplifier 94, an insulating section 95, a return electrode connector 99, an impedance detector 98, a rectifying and smoothing section 97, an A/D converter 96, an operation panel 90, and a monitor control switch 91. The control section 92 is the same as that of the first embodiment except that the control section 92 carries out the following control in response to the manipulation of the monitor control switch 91.

The operation of the second embodiment will briefly be described referring to FIG. 10. The operation panel 90 in FIG. 10 is provided with the monitor control switch 91 as an operation inhibiting switch to allow a user to manually disable the return electrode separation monitor. When the user depresses this monitor control switch 91, the control section 92 detects this event and determines that an instruction to disable the operation of the return electrode separation monitor has been given, and does not send a power enable signal, which enables the AC power supply 93 for impedance detection, to the AC power supply 93, thus disabling the AC power supply 93. This control inhibits detection of the contact impedance between the return electrode 71 and a patient, thus preventing the detection of separation of the return electrode, and can allow for a high-frequency output.

Since the above-described return electrode separation monitor for an electrosurgical apparatus according to the invention can monitor the separation state of the return electrode 71 from the rate of a change in contact impedance detection signal even when the contact impedance varies from one patient to another, monitoring according to the separation state of the return electrode 71 can be conducted directly, thus reducing a variation in the separation area of the return electrode 71, patient by patient, at the time an alarm is generated.

Further, the reference value which is used to compute the rate of a change is replaced with a latest reference value which is then stored, as needed, when the detected contact impedance detection signal becomes higher than the reference value and/or when the abnormal state, once determined as such in the difference detecting process, is returned to the normal state again later. Even with respect to a change in contact impedance with time or a sudden change in impedance which may occur when the abnormal state is returned to the normal state, the separation state of the return electrode can always be monitored with the optimal reference value, so that the detection precision can be improved.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalent.

I claim:

1. An electrosurgical apparatus for detecting separation of a return electrode of said electrosurgical apparatus for cutting and coagulating an organic tissue from a patient, comprising:

an impedance detecting section for detecting a contact impedance between said return electrode and said patient and generating an impedance detection signal corresponding to said contact impedance;

a first discrimination section for discriminating if said impedance detection signal generated by said impedance detecting section falls within a normal range of said contact impedance having predetermined upper and lower limits after said electrosurgical apparatus is powered on;

a storage section for, when said first discrimination section detects that said impedance detection signal lies in said normal range, storing the then impedance detection signal as a reference signal; and a second discrimination section for discriminating if said return electrode is in an abnormal state where said return electrode is separated from said patient, based on a difference between said impedance detection signal, generated by said impedance detecting section, and said reference signal stored in said storage section.

2. The electrosurgical apparatus according to claim 1, further comprising a reference signal replacing section for comparing said impedance detection signal, generated by said impedance detecting section, with said reference signal stored in said storage section and replacing said reference signal stored in said storage section with a then detected impedance detection signal, in accordance with a result of comparison.

3. The electrosurgical apparatus according to claim 2, wherein even when said second discrimination section has discriminated an abnormal state and thereafter discriminates that said abnormal state has been returned to a normal state, said reference signal replacing section replaces said reference signal stored in said storage section with a then detected impedance detection signal.

4. The electrosurgical apparatus according to claim 1, further comprising a reference signal replacing section for, when said second discrimination section has discriminated an abnormal state and thereafter discriminates that said abnormal state has been returned to a normal state, replacing said reference signal stored in said storage section with a then detected impedance detection signal.

5. The electrosurgical apparatus according to claim 1, further comprising a control switch for inhibiting an operation of the impedance detecting section.

6. An electrosurgical apparatus for detecting separation of a return electrode of said electrosurgical apparatus for cutting and coagulating an organic tissue from a patient, comprising:

an AC signal source for providing said return electrode with an AC signal for detecting a contact impedance between said return electrode and said patient;

an impedance detecting section for detecting said contact impedance between said return electrode and said patient and generating an impedance detection signal corresponding to said contact impedance;

an insulating interface section for electrically insulating said impedance detection signal generated by said impedance detecting section, and transferring said impedance detection signal to an internal circuit;

a first signal converting section for converting said impedance detection signal, transferred via said insulating interface section, to a DC signal;

a second signal converting section for converting said DC signal, converted by said first signal converting section, to digital data;

a storage section for storing said digital data converted by said second signal converting section; and a control section for controlling said electrosurgical apparatus, said control section having a first discrimination function for discriminating if digital data equivalent to said impedance detection signal stored in said storage section falls within a normal range of said contact impedance having predetermined upper and lower limits after said electrosurgical apparatus is powered on, a storage function for, when it is detected by said first discrimination function that said digital data lies in said normal range, storing the then digital data as a reference signal in said storage section, a comparison function for comparing digital data equivalent to said impedance detection signal generated by said impedance detecting section with said reference signal stored in said storage section, a replacing function having at least one of a first mode for replacing said reference signal with digital data equivalent to the then detected impedance detection signal based on a result of comparison by said comparison function, as needed, and a second mode for, when first discrimination function has discriminated an abnormal state and thereafter discriminates that said abnormal state has been returned to a normal state, replacing said reference signal with digital data equivalent to the then detected impedance detection signal, as needed, and a second discrimination function for discriminating if said return electrode is in an abnormal state where said return electrode is separated from said patient, based on a difference between digital data equivalent to said impedance detection signal, generated by said impedance detecting section, and said reference signal stored in said storage section.

7. The electrosurgical apparatus according to claim 6, wherein said impedance detecting section comprises:

a first transformer with a primary winding and a secondary winding, for transmitting an AC signal for detecting a contact impedance;

a return electrode connector for connection of said return electrode;

a second transformer having a primary winding and a secondary winding, for detecting said contact impedance and transferring a detection signal to the insulating interface section in an insulated manner;

a capacitor connected in parallel to said second transformer and constituting a parallel resonance circuit with said windings of said second transformer, said return electrode connector and said parallel resonance circuit being connected in series to said AC signal source, whereby said contact impedance is detected by voltage division with a fixed AC impedance of said parallel resonance circuit and said contact impedance.

8. A return electrode separation monitor adapted to be connected to an electrosurgical apparatus for detecting separation of a return electrode of said electrosurgical apparatus for cutting and coagulating an organic tissue from a patient, said monitor comprising:

an impedance detecting section for detecting a contact impedance between said return electrode and said patient and generating an impedance detection signal corresponding to said contact impedance;

a first discrimination section for discriminating if said impedance detection signal generated by said impedance detecting section falls within a normal range of said contact impedance having predetermined upper and lower limits after said electrosurgical apparatus is powered on;

a storage section for, when said first discrimination section detects that said impedance detection signal lies in said normal range, storing the then impedance detection signal as a reference signal; and a second discrimination section for discriminating if said return electrode is in an abnormal state where said return electrode is separated from said patient, based on a difference between said impedance detection signal, generated by said impedance detecting section, and said reference signal stored in said storage section.

9. A return electrode separation monitor adapted to be connected to an electrosurgical apparatus for detecting separation of a return electrode of said electrosurgical apparatus for cutting and coagulating an organic tissue from a patient, said monitor comprising:

an AC signal source for providing said return electrode with an AC signal for detecting a contact impedance between said return electrode and said patient;

an impedance detecting section for detecting said contact impedance between said return electrode and said patient and generating an impedance detection signal corresponding to said contact impedance;

an insulating interface section for electrically insulating said impedance detection signal generated by said impedance detecting section, and transferring said impedance detection signal to an internal circuit;

a first signal converting section for converting said impedance detection signal, transferred via said insulating interface section, to a DC signal;

a second signal converting section for converting said DC signal, converted by said first signal converting section, to digital data;

a storage section for storing said digital data converted by said second signal converting section; and a control section for controlling said electrosurgical apparatus, said control section having a first discrimination function for discriminating if digital data equivalent to said impedance detection signal stored in said storage section falls within a normal range of said contact impedance having predetermined upper and lower limits after said electrosurgical apparatus is powered on, a storage function for, when it is detected by said first discrimination function that said digital data lies in said normal range, storing the then digital data as a reference signal in said storage section, a comparison function for comparing digital data equivalent to said impedance detection signal generated by said impedance detecting section with said reference signal stored in said storage section, a replacing function having at least one of a first mode for replacing said reference signal with digital data equivalent to the then detected impedance detection signal based on a result of comparison by said comparison function, as needed, and a second mode for, when first discrimination function has discriminated an abnormal state and thereafter discriminates that said abnormal state has been returned to a normal state, replacing said reference signal with digital data equivalent to the then detected impedance detection signal, as needed, and a second discrimination function for discriminating if said return electrode is in an abnormal state where said return electrode is separated from said patient, based on a difference between digital data equivalent to said impedance detection signal, generated by said impedance detecting section, and said reference signal stored in said storage section.

10. A method of detecting separation of a return electrode of an electrosurgical apparatus for cutting and coagulating an organic tissue from a patient, comprising:

an impedance detecting step of detecting a contact impedance between said return electrode and said patient and generating an impedance detection signal corresponding to said contact impedance;

a first discrimination step of discriminating if said generated impedance detection signal falls within a normal range of said contact impedance having predetermined upper and lower limits after said electrosurgical apparatus is powered on;

a storage step of, when it is detected that said impedance detection signal lies in said normal range, storing the then impedance detection signal as a reference signal; and a second discrimination step of discriminating if said return electrode is in an abnormal state where said return electrode is separated from said patient, based on a difference between said impedance detection signal, generated in said impedance detecting step, and said reference signal stored in said storage step.

11. A return electrode separation detecting method of cutting and coagulating an organic tissue using an electrosurgical apparatus comprising an impedance detecting section for detecting contact impedance between return electrode and patient and generating an impedance detection signal corresponding to said contact impedance; an insulating interface section for electrically insulating said impedance detection signal generated by said impedance detecting section, and transferring said impedance detection signal to an internal circuit; a first signal converting section for converting said impedance detection signal, transferred via said insulating interface section, to a DC signal; a second signal converting section for converting said DC signal, converted by said first signal converting section, to digital data; a storage section for storing said digital data converted by said second signal converting section; and a control section for controlling said electrosurgical apparatus, said method comprising:

a first discrimination step of discriminating if digital data equivalent to said impedance detection signal stored in said storage section falls within a normal range of said contact impedance having predetermined upper and lower limits after said electrosurgical apparatus is powered on;

a storage step of, when it is detected in said first discrimination step that said digital data lies in said normal range, storing the then digital data as a reference signal in said storage section;

a comparison step of comparing digital data equivalent to said impedance detection signal generated by said impedance detecting section with said reference signal stored in said storage section;

a replacing step of executing replacement in at least one of a first mode for replacing said reference signal with digital data equivalent to the then detected impedance detection signal based on a result of comparison by said comparison step, as needed, and a second mode for, when first discrimination step has discriminated an abnormal state and thereafter discriminates that said abnormal state has been returned to a normal state, replacing said reference signal with digital data equivalent to the then detected impedance detection signal, as needed; and a second discrimination step of discriminating if said return electrode is in an abnormal state where said return electrode is separated from said patient, based on a difference between digital data equivalent to said impedance detection signal, generated by said impedance detecting section, and said reference signal stored in said storage section.

* * * * *